(12) United States Patent
Jinno et al.

(10) Patent No.: US 7,850,563 B2
(45) Date of Patent: *Dec. 14, 2010

(54) POWER TRANSMISSION MECHANISM AND MANIPULATOR

(75) Inventors: Makoto Jinno, Tokyo (JP); Toyomi Miyagawa, Kanagawa-Ken (JP); Shiro Tsukada, Kanagawa-Ken (JP); Akira Kudo, Kanagawa-Ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 241 days.

This patent is subject to a terminal disclaimer.

(21) Appl. No.: 11/927,765

(22) Filed: Oct. 30, 2007

(65) Prior Publication Data

US 2008/0051815 A1 Feb. 28, 2008

Related U.S. Application Data

(63) Continuation of application No. 10/811,848, filed on Mar. 30, 2004, now Pat. No. 7,300,373.

(30) Foreign Application Priority Data

Mar. 31, 2003 (JP) .............................. 2003-096446

(51) Int. Cl.
F16H 7/06 (2006.01)
(52) U.S. Cl. ..................... 474/153; 474/148; 474/152; 474/174
(58) Field of Classification Search ............. 474/64–70, 474/144, 148, 152–156, 174; 124/25.6, 86–90; 355/55, 71; 606/45, 130, 149, 170, 248; 600/1; 74/490.05, 490.06; 700/262, 253, 700/245; 345/156; 411/98, 778–781, 385, 411/400
See application file for complete search history.

(56) References Cited

U.S. PATENT DOCUMENTS

| | | | |
|---|---|---|---|
| 3,993,277 A | 11/1976 | Harley | |
| 4,201,177 A | 5/1980 | Holman et al. | |
| 4,241,715 A | 12/1980 | Jennings | |
| 4,294,233 A | 10/1981 | Takahashi | |
| 5,055,056 A | 10/1991 | Auclair et al. | |

(Continued)

FOREIGN PATENT DOCUMENTS

JP  49-12400  2/1974

(Continued)

*Primary Examiner*—Marcus Charles
(74) *Attorney, Agent, or Firm*—Oblon, Spivak, McClelland, Maier & Neustadt, L.L.P.

(57) ABSTRACT

A power transmission mechanism comprising: a flexible power transmission element; a pair of a drive pulley and a driven pulley on which the flexible power transmission element is wound, each the pulley having a pin-embedding hole formed to extend from the outer circumferential thereof toward the center thereof, and a slit elongated in the circumferential direction of the pulley to extend to opposite sides of the embedding hole and communicating with the embedding hole; and a pair of columnar or tapered anchor pins each having a path hole penetrating the anchor pin across the lengthwise direction thereof to receive the flexible power transmission element inserted therein, wherein each the anchor pin receiving the flexible power transmission element in the path hole thereof is embedded in the embedding hole of the associated pulley under pressure, and the flexible power transmission element is thereby held on the pulley.

7 Claims, 17 Drawing Sheets

U.S. PATENT DOCUMENTS

| | | |
|---|---|---|
| 5,697,355 A | 12/1997 | Schaffer |
| 5,797,900 A | 8/1998 | Madhani et al. |
| 6,394,998 B1 * | 5/2002 | Wallace et al. ................. 606/1 |
| 6,853,879 B2 | 2/2005 | Sunaoshi |
| 6,889,166 B2 | 5/2005 | Jinno |
| 6,936,042 B2 * | 8/2005 | Wallace et al. ................. 606/1 |
| 6,993,413 B2 | 1/2006 | Sunaoshi |
| 6,994,716 B2 | 2/2006 | Jinno |
| 7,043,338 B2 | 5/2006 | Jinno |
| 2004/0266574 A1 | 12/2004 | Jinno |
| 2005/0222587 A1 | 10/2005 | Jinno |
| 2005/0234434 A1 | 10/2005 | Sunaoshi |
| 2006/0079889 A1 * | 4/2006 | Scott .......................... 606/45 |
| 2006/0279534 A1 * | 12/2006 | Powers et al. ................ 345/156 |
| 2007/0142969 A1 * | 6/2007 | Devengenzo et al. ........ 700/245 |

FOREIGN PATENT DOCUMENTS

| | | | |
|---|---|---|---|
| JP | 51-1793 | | 6/1974 |
| JP | 50-148750 | | 11/1975 |
| JP | 62-113902 | | 5/1987 |
| JP | 02-110444 A | | 4/1990 |
| JP | 2-137521 | | 11/1990 |
| JP | 4-82688 | | 3/1992 |
| JP | 05-333448 A | | 12/1993 |
| JP | 2519749 | | 7/1996 |
| JP | 10-107954 A | | 4/1998 |
| JP | 11-282094 | | 10/1999 |
| JP | 2000-350735 | | 12/2000 |
| JP | 3278840 | | 2/2002 |
| JP | 2002-102248 | | 4/2002 |
| JP | 2002-339942 | | 11/2002 |
| JP | 2003-061969 A | * | 3/2003 |
| JP | 2003-167301 A | | 6/2003 |
| WO | WO 92/22723 | | 12/1992 |

* cited by examiner

POWER TRANSMISSION MECHANISM AND MANIPULATOR

CROSS-REFERENCE TO RELATED APPLICATION

This application a is continuation of U.S. application Ser. No. 10/811,848, filed Mar. 30, 2004, now U.S. Pat. No. 7,300, 373, and based upon and claims the benefit of priority from prior Japanese Patent Application No. 2003-96446, filed on Mar. 31, 2003, the entire contents of which are incorporated herein by reference.

BACKGROUND OF THE INVENTION

1. Field of the Invention

The present invention relates to a manipulator such as an operation-aiding manipulator or a manipulator for repairing a narrow portion of an energy device or the like. Especially, the present invention is intended to provide a power transmission mechanism using a wire and pulleys, which can be reduced in size and can be enhanced in reliability, rigidity and user-friendliness.

2. Related Background Art

In conventional laparoscope-assisted surgery such as laparoscopic cholecystectomy, a laparoscope 161, forceps 171, 172, etc. are inserted into an abdominal cavity through trocars 154 set in small incisions 151, 152, 153 made in the abdomen of a patient 150. Then, an operator (normally a surgeon) 160 conducts operation while watching the image acquired by the laparoscope on a monitor 162 as shown in FIG. 31. Since this type of operation does not need to open the abdomen, physical burden on the patient is alleviated, and the time required for recovery and discharge from the hospital after operation is greatly reduced. Therefore, its adaptation to wider fields of application is expected.

Under the background, the Inventors already proposed a medical manipulator combining a robot technique to conventional forceps (robot forceps) 1 as shown in FIG. 32 (Japanese Patent Laid-open JP-2000-350735A). This manipulator 1 includes a control command unit 20 having an attitude control unit 23 and a treatment control unit 24; a connector unit 30 having one end connected to the control command unit 20; a work unit 10 connected to the other end of the connecting unit 30 and having a treatment unit 14 and supports 15 and 16 supporting the treatment unit 14 to allow them to change in attitude in at least two degrees of freedom of motion; and a controller (not shown) for delivering a control command from the attitude control unit 23 to the supports to change the attitude of the treatment unit 14 and for delivering a control command from the treatment control unit 24 to the treatment unit 14 to activate it.

The Inventors also proposed a medical manipulator as shown in FIG. 33 as another arrangement and degrees of freedom suitable for suture and ligature (Japanese Patent Laid-open JP-2002-102248A). This medical manipulator 1 includes a work section 10, a control command unit 20, and a connector unit 30 having opposite ends connected to the work unit 10 and the control command unit 20 respectively. In the work section 10, a support unit, having a first rotation axis 11 intersecting the axial direction 31 of the connector unit 30 and a second axis 12 intersecting the first rotation axis 11, and a treatment unit (gripper) 14 for working on the target site of surgery are aligned along the second rotation axis 12. In other words, the work section 10 has a yawing-axis joint support 15 and a rolling-axis joint support 16 that function to support the gripper 14 to allow them to change in attitude in two degrees of freedom of motion. The control command unit 20 includes: an attitude control unit 23 having a third rotation axis 21 intersecting the center-axial direction 31 of the connector unit 30 and a fourth rotation axis 22 intersecting the third rotation axis 21; and a treatment control unit 24 gripped and operated by an operator whose wrist will rotate approximately in parallel to the fourth rotation axis 22. The gripping motion 13 of the treatment unit 14 for working on the target site of surgery is given by the gripping motion 25 of the treatment control unit 24.

In comparison with a remote-control master/slave manipulator, the robot forceps conjoin the control unit (master) and the forceps end hand (slave) to combine both an advantage of conventional forceps, namely enabling large and quick motions which will be effected more easily and reliably by the operator, and an advantage of a manipulator, namely, enabling minute works or controls from difficult angles. Since the robot forceps have joints for twists, rotations, and other motions, at the end, they can change the attitude of the hand freely, and make suture and ligature from various directions easier, which have been difficult with conventional forceps. The robot forceps can be used together with conventional surgical appliances, for example, by handling the robot forceps with the right hand and handling conventional forceps with the left hand. Additionally, because of the simple and compact system, the robot forceps can be introduced at a low cost.

Furthermore, manipulators having this type of configuration are suitable also for works at locations difficult for the operator to work directly at the very site, such as repair works of narrow portions of energy devices. It will be needless to say that the size (length, thickness, dimension, etc.) of the manipulator will be determined depending upon the nature of the intended work and the region of the work. Therefore, the robot forceps are not limited to the medical use.

Surgery-assisting manipulators and manipulators for repairing narrow portions in energy devices, etc. are required to be compact, lightweight, durable, easy to operate, precisely responsive to intended works and inexpensive. To meet these requirements, their power transmission mechanisms must be compact, lightweight, reliable, durable and inexpensive. Especially in the manipulators of the configurations shown in Japanese Patent Laid-open Publications JP2000-350735A and JP2002-102248A, because of the restriction by the unitary structure of the master and the slave, their shapes, sizes, arrangements of the power transmission mechanisms largely affect how they are easy to operate.

In robot and electromechanical devices and apparatuses including manipulators, power transmission for transmitting the power of an actuator to an end effector (such as a hand or tool) generally relies on wires and pulleys. In case a motion range of many revolutions is required in a power transmission mechanism using a wire and pulleys, it is usual to wind the wire 52 on pulleys 50, 51 as shown in FIG. 22 to transmit power by frictional force. To obtain a large transmission torque, a large frictional force is required. For this purpose, the wire may be wound on the pulleys over a larger angle or multiply, or the tensile force of the wire may be increased. In any of these cases, however, since the drive force basically relies on friction, a decrease of the tensile force, which may occur upon expansion of the wire, causes slips between the wire and the pulleys, and this invites a decrease of the torque. To cope with this problem, a tension adjusting mechanism is sometimes added. Therefore, it complicates the mechanism, and increases the size and the cost of the device. Furthermore, it invites a decrease of the rigidity of the joints. Furthermore, to wind the wire multiply on the pulleys, the pulleys must be wide enough to accommodate the multiple turns of the wire, and invite an increase of the device size. Usually, surgery-assisting manipulators and manipulators for repairing narrow portions of energy devices, by nature, do not have ample spaces for multiply winding a wire. On the other hand, to hold the wire on the pulleys, a fastening member 53A is usually used as shown in FIG. 23. However, in case the wire is multiply wound on the pulleys, the motion range (rotation angle) is usually limited to less than 180 degrees because of interference between the fastening member and the wire. There are some methods of increasing the winding angle as disclosed in the publication of Japanese Patent No. 2,519, 749. However, the maximum angle is about 270 degrees, and it is difficult to enable rotation of 360 degrees or more. As far as the rotation range of pulleys is limited, the motion range of the manipulator joint, i.e. the work range of the end effector, remains narrow and will disturb the work by the operator. Thus, the manipulator largely degrades in fidelity to intended works and controllability. To assure an ample work region not disturbing the works, the manipulator needs the largest possible number of rotation, but this is difficult with conventional power transmission mechanisms.

On the other hand, in the power transmission mechanism using a wire and pulleys as shown in FIG. 24, in case the wire diameter is small or the drive pulley and the driven pulley are apart by a long distance, influence of elastic deformation (expansion) of the wire may increase and disable transmission of sufficient power. In addition, there is the problem that sufficient rotational rigidity is not obtained at the driven shaft (output shaft) in a hold mode where the drive pulley is stationary or in a servo lock mode. If the desired rotational rigidity is not obtained, then the manipulator degrades in controllability and fidelity to intended works, and operator cannot perform sufficient works.

In the master-slave combined manipulator conjoining the master and the slave as shown in FIGS. 25 and 27, eccentric mass about the connector unit 30 is usually produced. Depending upon the location of the eccentric mass, rotational torque out of the operator's intention may be produced by the weight about the connector unit, which degrades the controllability. Especially in the initial status at the start of controls or in the basic attitude of the manipulator, which is the most standard attitude for controls, if rotational torque is produced by eccentric mass about the connector unit, it will impose useless load to the operator and may invite significant degradation of controllability. In addition, in the manipulator having the common rolling axis, pitching axis and rolling axis as shown in FIG. 25, it is difficult to change the attitude of the work section to the yawing direction (lateral or right-and-left direction) from the basic attitude illustrated because it is the change of attitude to the singular configuration. In the arrangement of degrees of freedom shown in FIG. 29, having the illustrated common rolling axis, yawing axis, rolling axis, it is difficult to change the attitude of the work section from the illustrated basic attitude to the pitching direction (vertical or up-and-down direction) because it is the change of attitude to the singular configuration. In actual controls of the manipulator, the attitude of the work section is changed more frequently to the lateral and vertical directions from the basic attitude. Therefore, the arrangement for degrees of freedom of motion shown in FIG. 25 or 29 will invite degradation of controllability.

SUMMARY OF THE INVENTION

It is therefore an object of the invention to reduce the size and enhance the reliability, rigidity and controllability of various kinds of manipulators.

According to an embodiment of the invention, there is provided a power transmission mechanism comprising: a flexible power transmission element; a pair of a drive pulley and a driven pulley on which the flexible power transmission element is wound, each said pulley having a pin-embedding hole formed to extend from the outer circumferential thereof toward the center thereof, and a slit elongated in the circumferential direction of the pulley to extend to opposite sides of the embedding hole and communicating with the embedding hole; and a pair of columnar or tapered anchor pins each holding the flexible power transmission element on the pair of pulleys, each said anchor pin having a path hole penetrating the anchor pin across the lengthwise direction thereof to receive the flexible power transmission element inserted therein, wherein each said anchor pin receiving the flexible power transmission element in the path hole thereof is embedded in the embedding hole of the associated pulley under pressure, and the flexible power transmission element is thereby held on the pulley.

According to another embodiment of the invention, there is provided a power transmission mechanism comprising: a flexible power transmission element; and a pair of a drive pulley and a driven pulley on which the flexible power transmission element is wound, wherein at least one of two spans of the flexible power transmission element spanning between the pair of pulleys is covered by a hollow elongate member, or cut and connected by a solid elongate member.

According to still another embodiment of the invention, there is provided a manipulator having a work unit, connector unit and a control unit to activate the work unit under a control command given from the control unit to the work unit through the connector unit, comprising: a power transmission mechanism for transmitting a control command from the control unit to the work unit; and a driving device for driving the power transmission mechanism, and having an eccentric mass about the connector unit, wherein the power transmission mechanism includes a flexible power transmission element, and a pair of a drive pulley and a driven pulley on which the flexible power transmission element is wound, and wherein the drive pulley and the driven pulley are oriented to make a twist between the rotation axes thereof to position the center of gravity of the driving device as the eccentric mass about the connector unit in a vertically lower area of the connector unit when the manipulator takes the basic attitude thereof.

According to the invention, the power transmission mechanism using a wire (flexible power transmission element) and pulleys requires no tension adjusting mechanism required in conventional frictional drive systems, and has the structure in which the wire does not interfere with the portion for firmly holding the wire on the pulleys. Therefore, the power transmission mechanism meets the requirements of space saving and multiple rotations. Further, the fastening force is enhanced by the wedge effect. Accordingly, the motion region of the manipulator junction, i.e. the work area of the end effector, is wide enough to allow smooth works. Therefore, the manipulator is greatly improved in fidelity to intended works and in controllability.

In addition, since at least one of two spans of the wire (the span of the wire subjected to higher tensile force) between the drive pulley and the driven pulley is covered by a hollow elongate member or connected by a solid elongate member, influence of elastic deformation (expansion) of the wire is small enough to assure transmission of sufficient power even when the wire is thin, or the drive pulley and the driven pulley are apart by a long distance. Further, in a hold mode where the drive pulley is stationary or in a servo lock mode, sufficient rotational rigidity is obtained at the driven shaft (output shaft). Therefore, reliable power transmission is assured, and the manipulator is greatly improved in fidelity to intended works and in controllability.

Moreover, since the manipulator has the configuration free from rotational torque caused by eccentric mass about the connector unit in the basic attitude of the manipulator, which is the most standard attitude in the initial status at the start of controls or during controls, the manipulator is enhanced in fidelity to intended works and in controllability without compelling the operator to exert useless control force. Furthermore, the degrees of freedom of motion have the common rolling axis by the connector unit, bent axis in the aslant direction between the yawing axis (lateral direction) and the pitching axis (vertical direction), and rolling axis. Therefore, it is easy to change the attitude of the work section from the basic attitude, and the manipulator is significantly improved in fidelity to intended works and in controllability.

That is, it is possible to provide a power transmission mechanism that is compact, lightweight, reliable, rigid and inexpensive, and by incorporating the power transmission mechanism, it is possible to provide a manipulator for assisting surgery or repairing narrow portion in energy devices, which is enhanced in controllability and in fidelity to intended works.

DETAILED DESCRIPTION OF THE INVENTION

Explained below are some embodiments of the invention with reference to the drawings.

Figure 1:
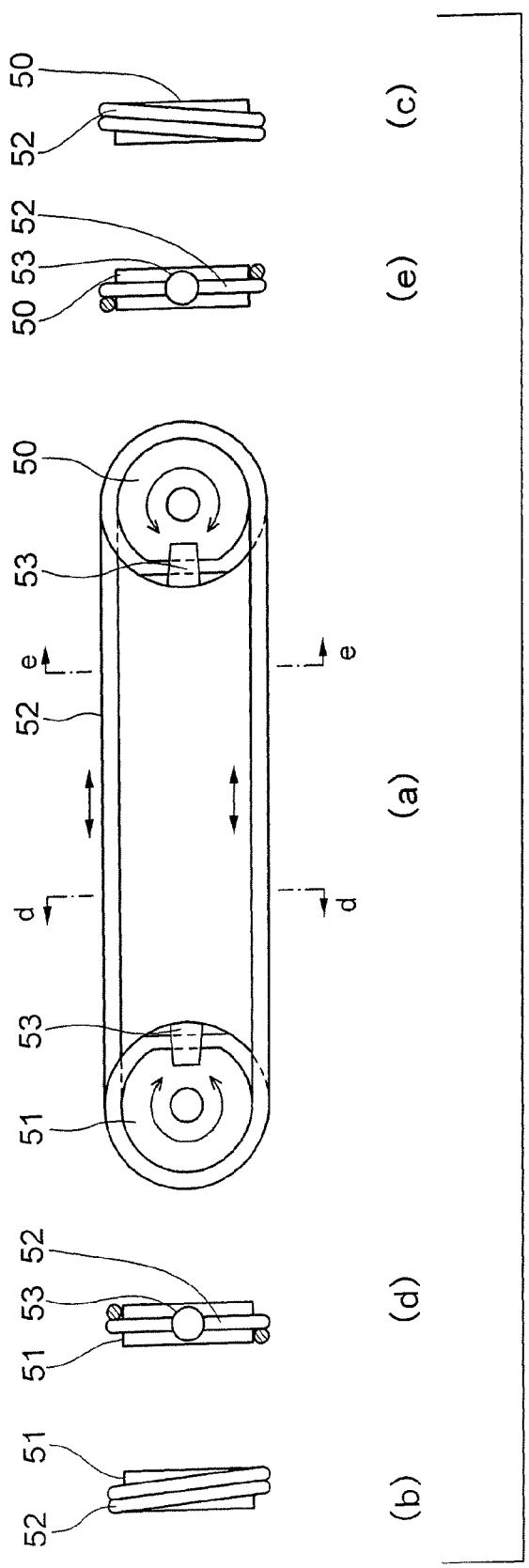
FIG. 1 is a set of a front elevation of a power transmission mechanism according to the first embodiment of the invention, its right and left side elevations, and its sectional views taken along the d-d line and e-e line.
Figure 2:
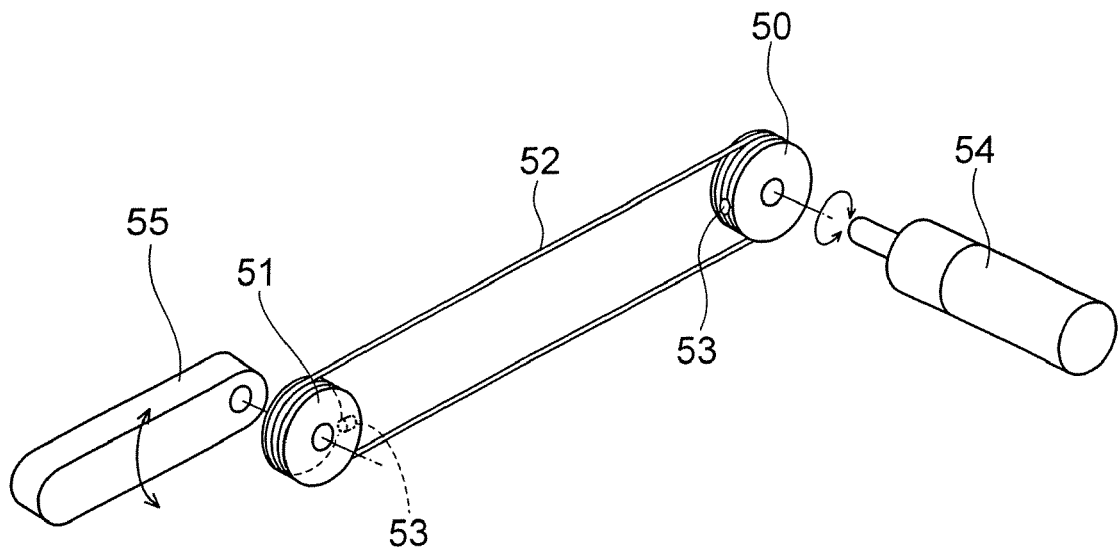
FIG. 2 is a schematic exploded perspective view showing the entirety of the power transmission system according to the first embodiment of the invention.
Figure 3:
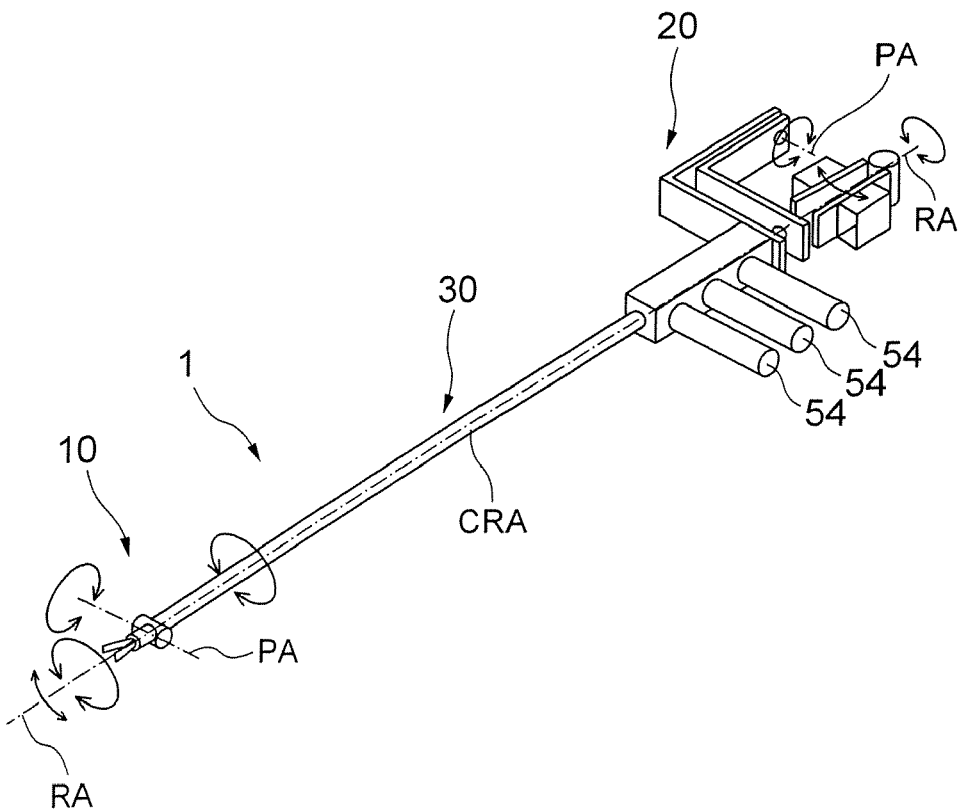
FIG. 3 is a schematic perspective view of a manipulator incorporating the power transmission mechanism according to the first embodiment of the invention.

FIG. 1 is a set of sectional views and side elevations showing the driving and driven wire/pulley portions in a power transmission mechanism according to the first embodiment of the invention. FIG. 2 is a schematic diagram of the entire power transmission system, with its components being exploded. FIG. 3 is a schematic diagram showing a manipulator incorporating the same power transmission mechanism.

As shown in FIG. 1, the power transmission mechanism of a manipulator according to the first embodiment of the invention includes a drive pulley 50, driven pulley 51, wire (flexible power transmission element) 52, columnar or tapered pin 53, and wire connecting member (not shown). The wire is usually a stainless wire rope, but a rope of any other material such as tungsten or fabric materials are usable without problems, provided it is elastic. In the present invention, the wire contemplates any of all these materials. The wire connecting member is an element necessary for connecting opposite ends of one linear wire to make a loop.

The wire 52 is loop-shaped, and it is wound on pulleys 50 51 by 1.5 turns respectively in this first embodiment. The wire 52 is firmly held on the pulleys 50, 51 by anchor pins 53 (fastening portions). In this configuration, the maximum motion range of ±270 degrees is obtained.

FIG. 2 shows an example of the entire power transmission system in which a motor 54 with a reducer is associated with the drive pulley 50 whereas an arm 55 is associated with the driven pulley 51. However, the system is not limited to this configuration. Basically, the system is a power transmission mechanism for transmitting power from the drive side to the driven side. Similarly, although FIG. 3 shows an example of incorporating the system in a manipulator 1, combination of the system and the manipulator 1 is not limited to this configuration. The manipulator 1 is composed of a work unit 10, control unit 20, connector unit 30, control unit (not shown), and others, and the operator adjusts the position and attitude of the work unit by controlling the controller. This manipulator is used for works in narrow portions or inserted through a narrow portion to work. Therefore, the work unit 10 must be compact. Additionally, for enhanced fidelity to intended works and operability, a sufficient motion region (rotation angle of the driven shaft) is required.

Figure 4:
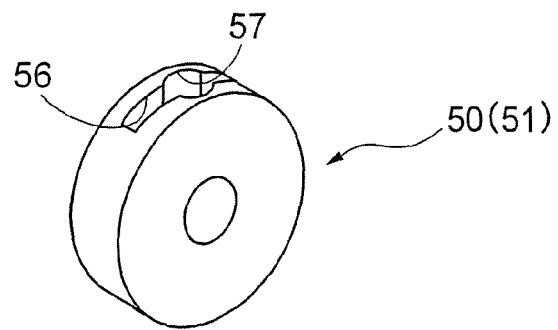
FIG. 4 is a perspective view of a pulley used in the power transmission mechanism according to the first embodiment of the invention.
Figure 5:
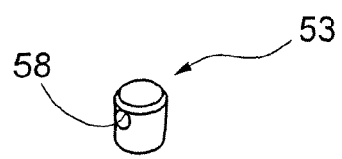
FIG. 5 is a perspective view of an anchor pin used in the power transmission mechanism according to the first embodiment of the invention.
Figure 6:
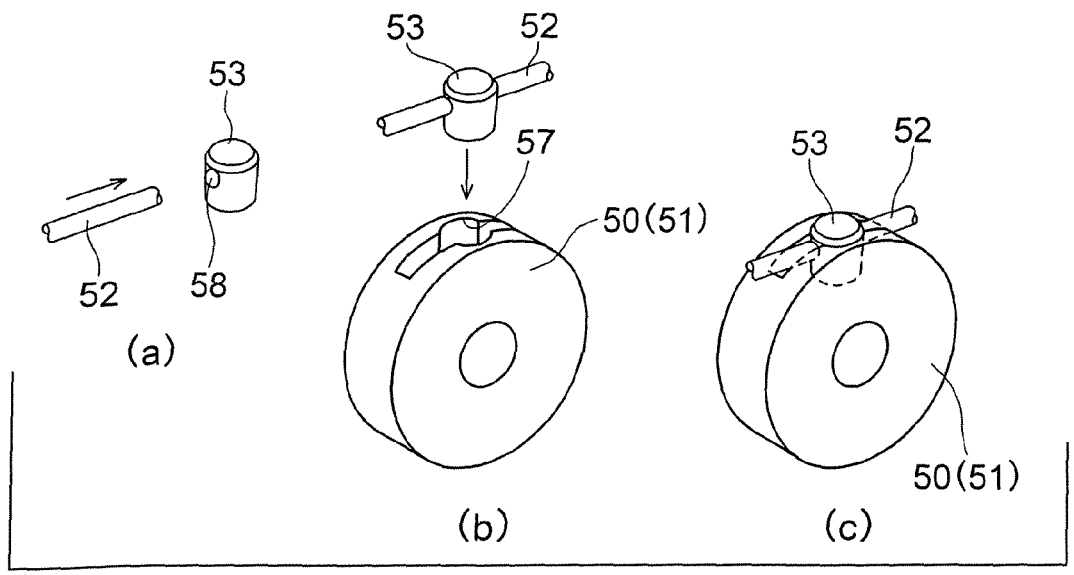
FIG. 6 is a set of diagrams showing an assembling procedure of the power transmission mechanism according to the first embodiment of the invention.

To illustrate details of the drive unit, FIG. 4 shows a perspective view of the pulley 50 or 51. Basically, the drive pulley 50 and the driven pulley 51 may be identical in structure. The pulley 50 has a slit 56 wide enough to receiving the wire and a columnar or tapered hole (embedding hole) 57 at a central position thereof. The hole 57 is formed to extend from the outer circumferential surface of the pulley 50, 51 toward its center, and the slit 56 communicates with the hole 57. FIG. 5 shows a perspective view of the anchor pin 53 for firmly holding the wire 12 on the pulley 50. The slit 56 is formed to extend laterally, i.e. in parallel with the tangential line of the circumferential surface of the pulley 50, 51. The anchor pin 53 has a columnar or tapered shape, and has a hole 58 extending across the anchor pin 53 and large enough to pass the wire approximately at its center. FIG. 6 is a set of diagrams (a) through (c) illustrating procedures for anchoring the anchor pin 53. After the wire is inserted through the hole 58 in its central location of the columnar or tapered anchor pin 53, the columnar or tapered anchor pin 53 is inserted in the columnar or tapered hole 57 of the pulley 50. Thus, the wire 52 is reliably held on the pulley 50. That is, the diameter of the anchor pin 53 is larger than the inner diameter of the hole 57 to be firmly held in the hole 57 by compression engagement. The anchor pin 53 is sized and shaped so that the top surface thereof becomes flush with the outer circumferential surface of the pulley 50. In this manner, even when the rotation angle is large, one turn of the wire does not interfere the other turns of the wire. Further, tapering one or both of the hole 57 and the anchor pin 53 assures firmer engagement of the wire 52 with the pulley 50 by a wedge effect. Therefore, it is possible to hold the wire 52 on the pulley 50 more firmly, multiple winding is also possible.

Figure 7:
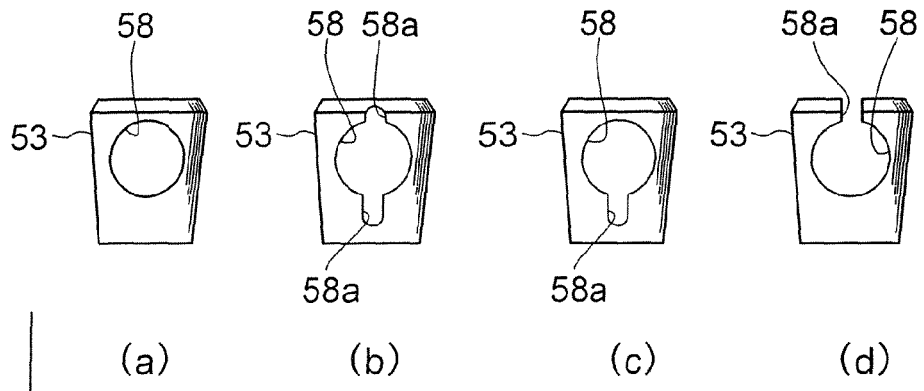
FIG. 7 is a set of diagrams showing various shapes of the anchor pin used in the power transmission mechanism according to the first embodiment of the invention.
Figure 8:
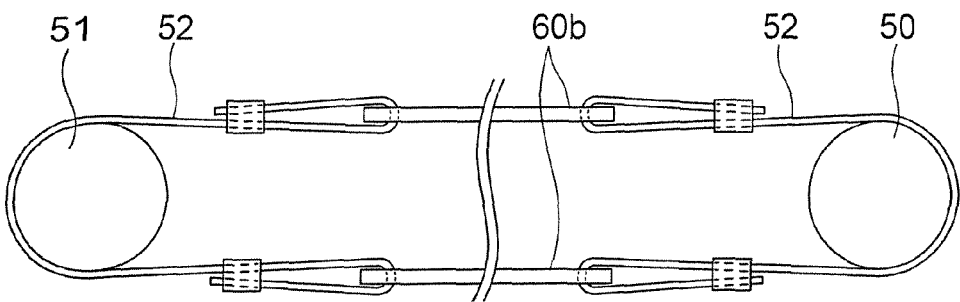
FIG. 8 is a front elevation of a power transmission mechanism according to the second embodiment of the invention.
Figure 9:
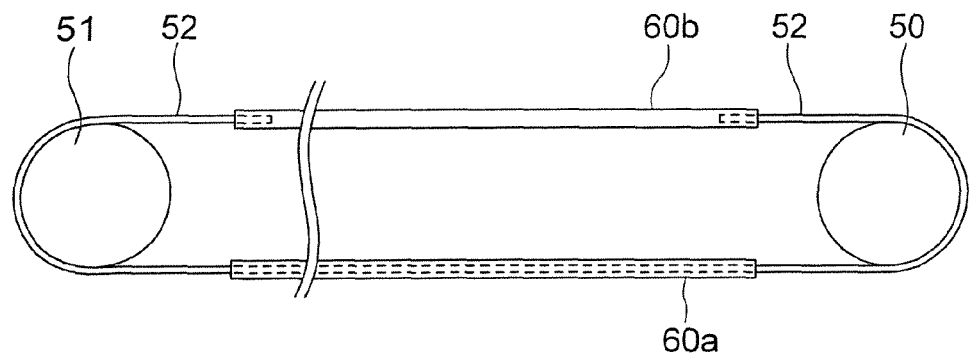
FIG. 9 is a front elevation of another type of power transmission mechanism according to the second embodiment of the invention.
Figure 10:
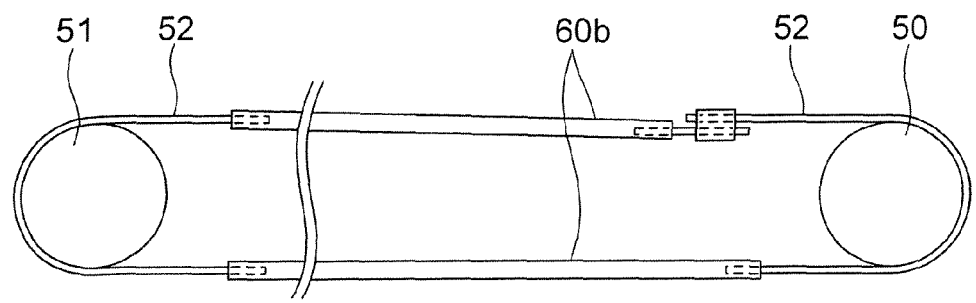
FIG. 10 is a front elevation of another type of power transmission mechanism according to the second embodiment of the invention.
Figure 11:
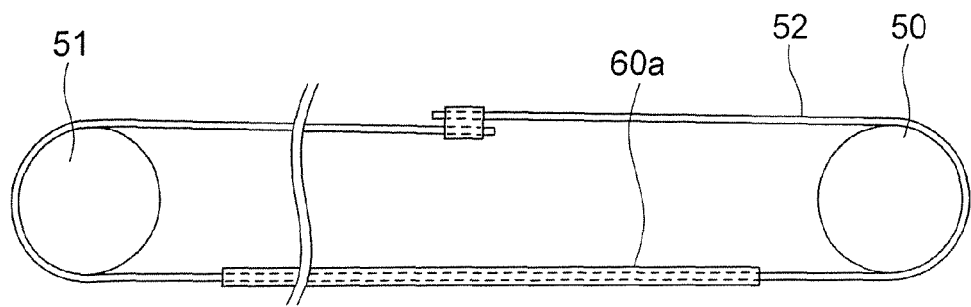
FIG. 11 is a front elevation of another type of power transmission mechanism according to the second embodiment of the invention.

FIG. 7 is a set of diagrams showing various shapes of the hole 8 that can be made in the tapered or columnar anchor pin 53. The anchor pin 53 is made of an elastic material, and reduces its diameter when compressed. The circular hole 58 shown at (a) can be made at a low cost. When the hole 58 includes a slit 58a for contraction of the anchor pin 53 as shown at (b) through (d) in FIG. 7, the hole 58 easily deforms and can efficiently transmit the compression force by the wedge effect. Therefore, the compression force further increases.

Moreover, in the instant embodiment of the invention, the assembly of the wire 52 to the pin 53 and the assembly of the pin 53 to the pulley 50 can be done simultaneously by inserting the pin 53 in to the tapered hole 57. Therefore, the labor effectiveness of the assembly is improved.

According to the first embodiment, since the power transmission mechanism using the wire 52 and the pulleys 50 551 needs no special mechanism for adjustment of the tensile force required in conventional frictional drive systems; different turns of the wire 52 do not interfere at the hold portions on the pulleys 50, 51; and the wedge effect exerts a strong fastening power. Therefore, wider extension is assured as the motion region of the manipulator's joint, namely, the work region of the end effector, which is large enough to assure smooth works with the manipulator. Thus, the manipulator is greatly enhanced in fidelity to intended works and in controllability.

FIGS. 8 through 12 are simplified sectional views of the wire/pulley portions at the drive side and the lower side in a power transmission mechanism of a manipulator according to the second embodiment of the invention. Here are shown examples of the use of a hollow tube (as a hollow elongate member, also in the description herein below) covering one or both of the spans of the wire 52 between the pulleys 50 and 51, or the use of a solid cord (or a solid rod, as a solid elongate member, also in the description herein below) connecting one or both of the spans of the wire 52 between the pulleys 50 and 51. As shown n these figures, there are various possible ways of connecting the wire 52 to the pulleys, and any of them is employable without problems. In the examples shown in FIG. 9 and FIG. 11, the wire 52 need not pass through the lower hollow tube 60a, but it may be secured to the hollow tube 60a at two or more different points. Since the pull strength of the portions of fixture is usually lower than the pull strength of the wire 52 itself, it is important to assure the reliable strength at the points of fixture. However, when the wire 52 is inserted all through the hollow tube 60a, the pull strength at least of the wire 52 is ensured. Therefore, breakage of the points of fixture by defective fixture (for example, fixture by pressure) can be prevented.

In FIGS. 8 through 11, at least one of two spans of the wire 52 subjected to higher tensile force (lower span of the wire) is connected by the solid cord 60b, or inserted in the hollow tube 60a. That is, one of two spans of the wire 52 (power transmission system) spanning between the pair of pulleys 50, 51, which is subjected to a higher tensile force, is reinforced by the hollow tube 60a or the solid cord 60b. As such, in case one of two spans of the wire 52 is subjected to higher tensile force (assume it be the lower span of the wire), sufficient effect will be obtained by inserting at least the span of the wire 52 subjected to higher tensile force through the hollow tube 60a or connecting it with the solid cord 60b.

Figure 12:
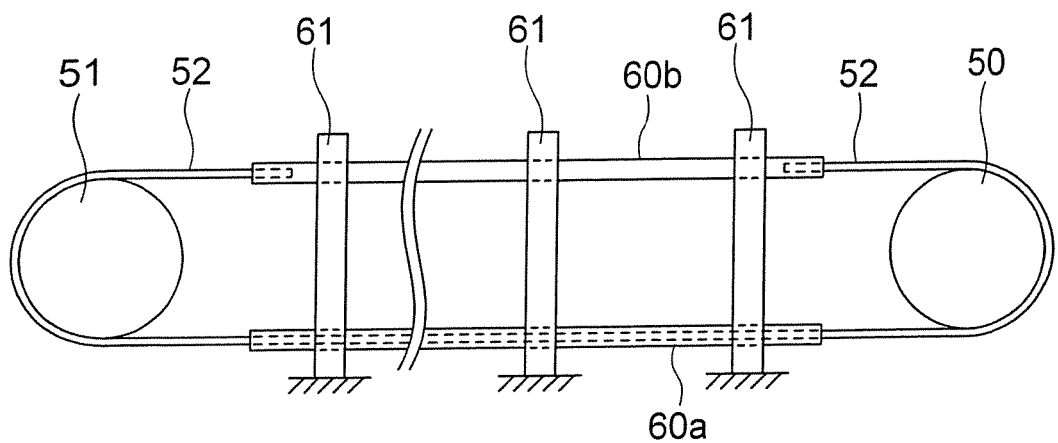
FIG. 12 is a front elevation of another type of power transmission mechanism according to the second embodiment of the invention.

FIG. 12 shows an example in which the hollow tube 60a, or the solid cord 60b, is supported in holes 61a, 61 of disk-shaped support members 61. In FIG. 12, each support member 61 has six holes 61a, 61, and two of them are used to insert and support the hollow tube 60a, or the solid cord 60b. The number of holes is determined by the number of drive axes.

Figure 13:
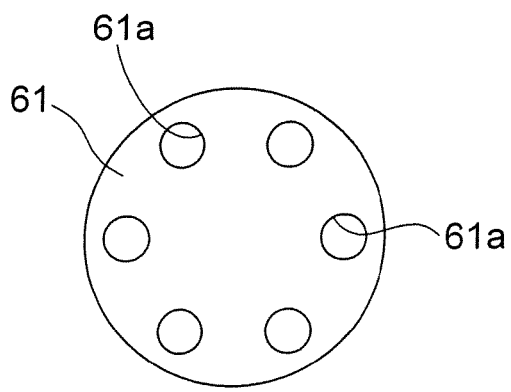
FIG. 13 is a front elevation of a support member used in the power transmission mechanism according to the second embodiment of the invention.
Figure 14:
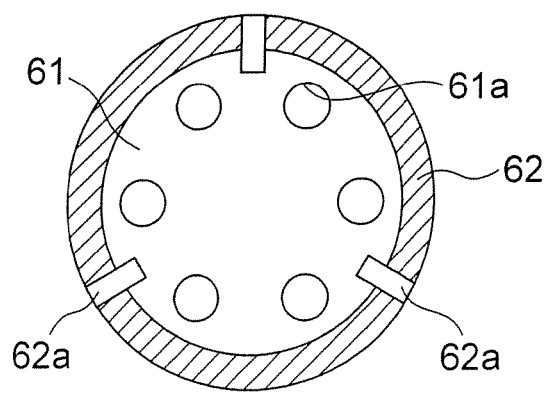
FIG. 14 is a transverse sectional view of the support member set in a pipe of the power transmission mechanism according to the second embodiment of the invention.

In the case where both spans of the wire 52 (upper and lower spans in the figure) are inserted in the hollow tubes 60a, or connected by the solid cords 60b, as far as the shafts of the drive pulley 50 and the driven pulley 51 are oriented perpendicularly, the upper and lower spans of the wire 52 having the hollow tubes 60a or the solid cords 60b are well balanced in gravity. Therefore, the gravity components of the hollow tube 60a or the solid cord 60b do not increase the drive torque. However, if both spans of the wire 52 lie to align on the same horizontal level, gravity of the hollow tube 60a or the solid cord 60b may exert non-negligible influences to the tensile force of the wire 52. In an extreme case, it invites an increase of the vibration or breakage of the wire. To cope with this problem, the use of the support members 61 to support the hollow tube 60a or solid cord 60b as shown in FIG. 12 contributes to reducing the influences of the gravity. In case the drive pulley 50 are formed in a pipe 62 as a part of the connector unit 30, the support members 61 as shown in FIG. 13 may be located and fixed at some positions in predetermined intervals inside the pipe 62 as shown in FIG. 14.

According to the second embodiment, since the at least one of two spans of the wire between the drive pulley 50 and the driven pulley 51, which is subjected to higher tensile force, is inserted in the hollow tube 60a or connected by the solid cord 61b, even when the wire 52 is thin, or the drive pulley 50 and the driven pulley 51 are apart by a log distance, it is possible to reduce the influence of the elastic deformation (expansion) of the wire 52 during transmission of power much enough to ensure transmission of sufficient power, and it is possible to obtain sufficient rotational rigidity at the driven shaft (output shaft) in the hold mode where the drive pulley is stationary or in the servo lock mode. Additionally, the support members can prevent unacceptable increase of vibration caused by the gravity of the hollow tube or solid rod and breakage of the wire. Therefore, the power transmission mechanism ensures reliable power transmission, and the manipulator is greatly enhanced in fidelity to intended works and in controllability.

FIGS. 15 through 20 are perspective views of manipulators according to the third embodiment of the invention and diagrams showing their wire/pulley portions. In the master-slave combined manipulator conjoining the master and the slave, the center of gravity of the driving device is remote from the connector unit 30. Therefore, eccentric mass about the connector unit 30 is produced in most cases. Depending upon the position of the eccentric mass, rotational torque out of the operator's intention may be produced about the connector unit 30 by influences of the gravity, and this may invite degradation of the controllability. Especially in the initial status at the start of controls of the manipulator or in the basic attitude of the manipulator, which is the most standard attitude for controls, if rotational torque is produced by eccentric mass about the connector unit, it will impose useless load to the operator and may invite significant degradation of controllability.

Figure 15:
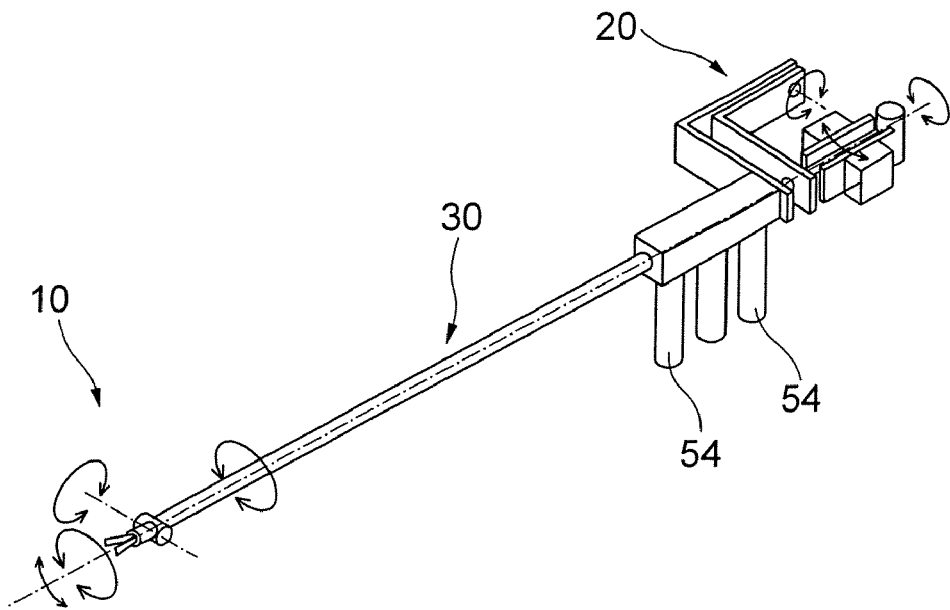
FIG. 15 is a perspective view of a manipulator according to the third embodiment of the invention.

In most cases, it is the drive motor 54 that has the mass occupying a great part. Tanking it into consideration, the manipulators shown in FIGS. 15 through 20 are configured to locate the center of gravity of the drive motor 54 below the connector unit 30 when the manipulator takes the basis attitude. That is, orientation of the drive pulley 50 is twisted with respect to the orientation of the driven pulley 51 in comparison with, for example, FIG. 6. Although the optimum basic attitude of the manipulator varies depending upon the work to be effected, FIG. 15 shows the degrees of freedom of motion including the common rolling axis (about the axis of the connector unit 30), pitching axis and the rolling axis.

Figure 16:
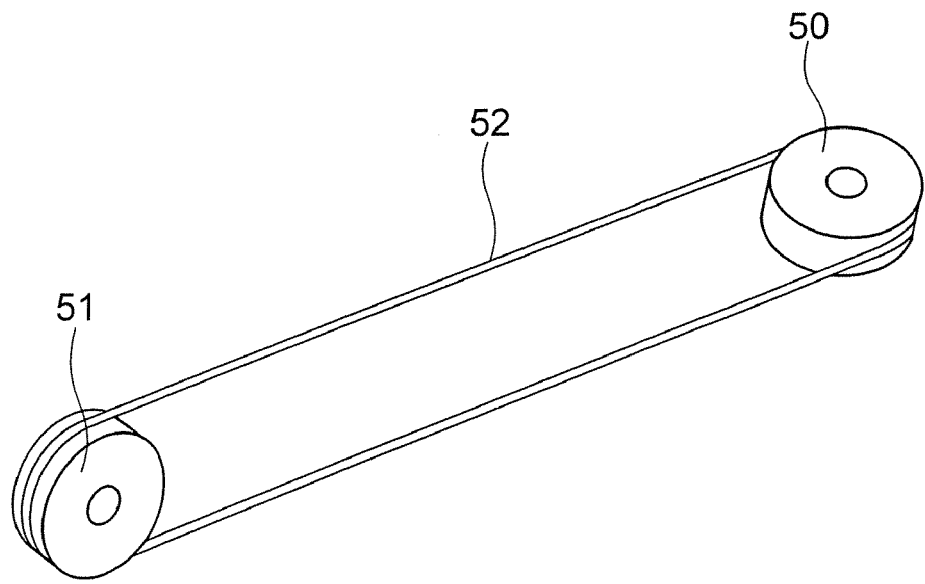
FIG. 16 is a perspective view of the manipulator according to the third embodiment of the invention, which illustrates a relation between a wire and pulleys.
Figure 17:
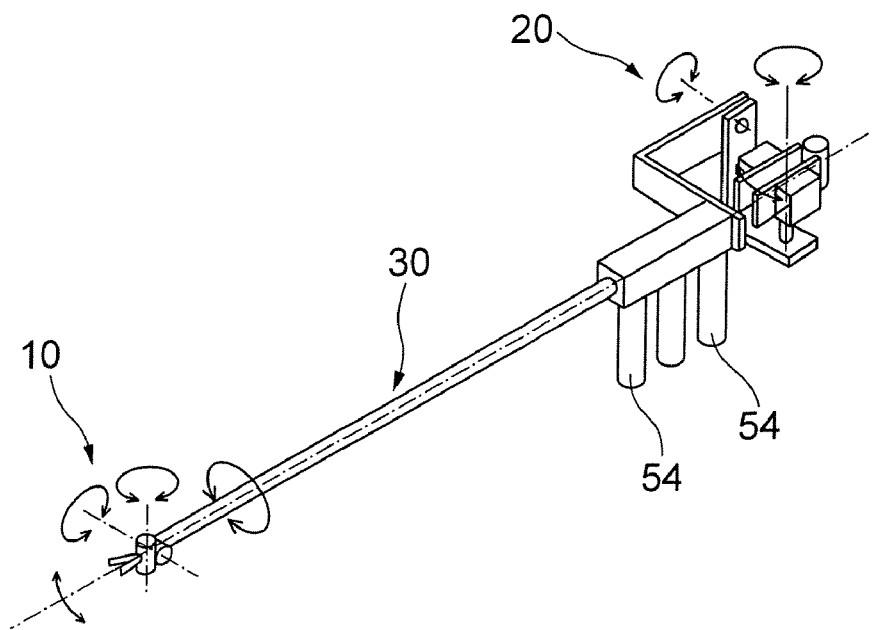
FIG. 17 is a perspective view of the manipulator according to the third embodiment.
Figure 18:
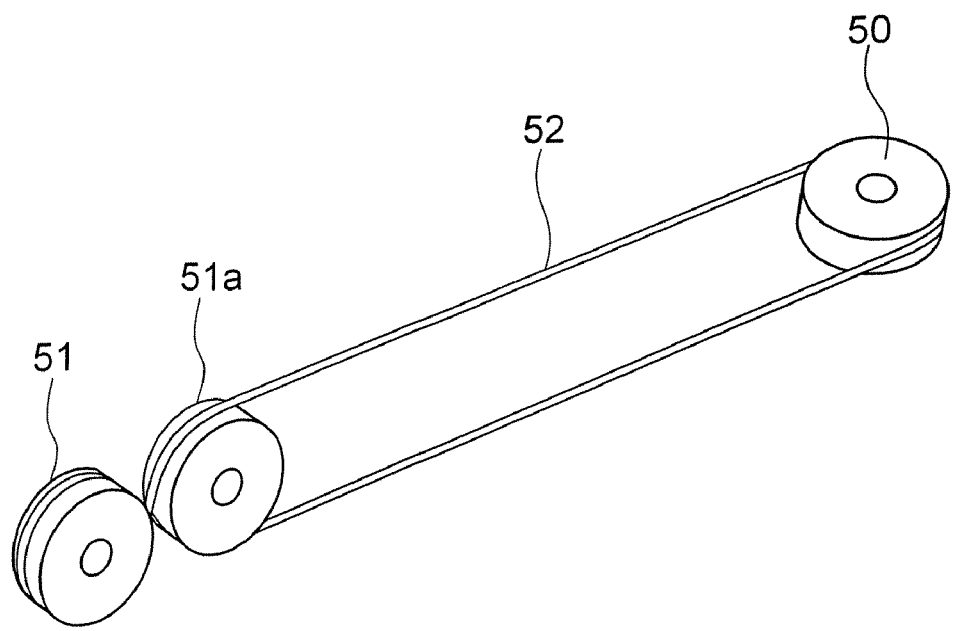
FIG. 18 is a perspective view of the manipulator according to the third embodiment of the invention, which illustrates a relation between the wire and pulleys.
Figure 25:
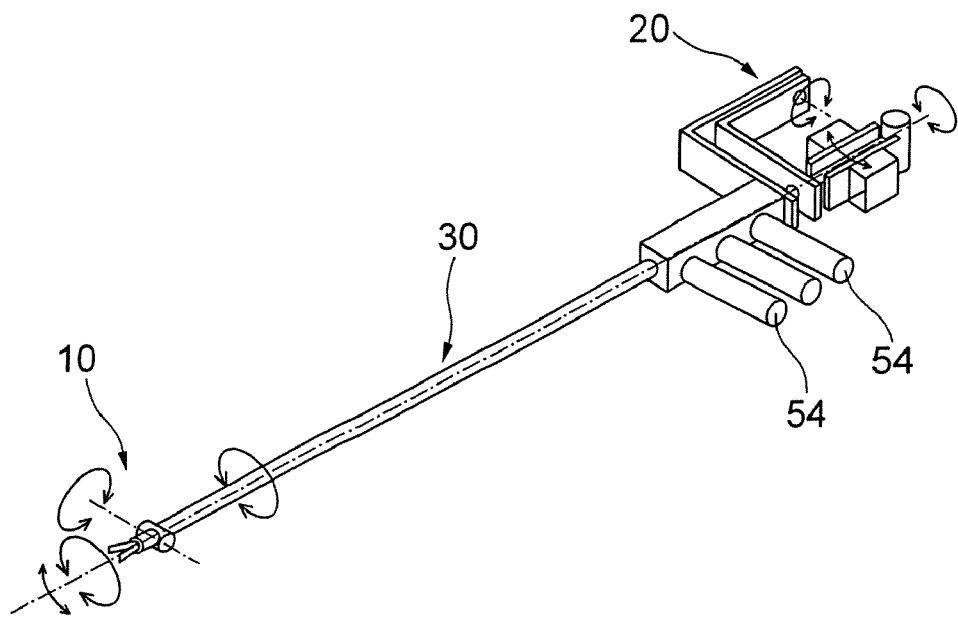
FIG. 25 is a perspective view of a conventional manipulator.
Figure 26:
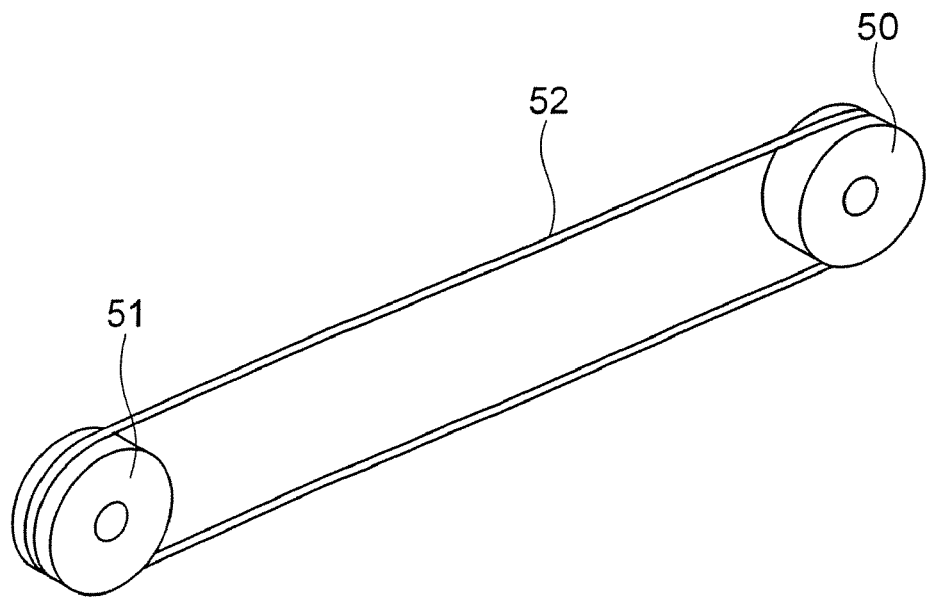
FIG. 26 is a perspective view of the conventional manipulator, which illustrates a relation between a wire and pulleys.
Figure 27:
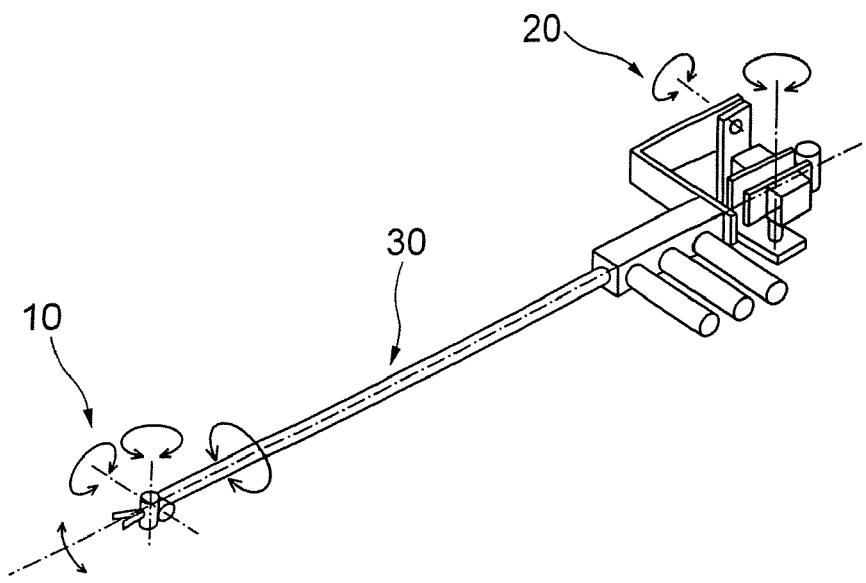
FIG. 27 is a perspective view of a conventional manipulator.
Figure 28:
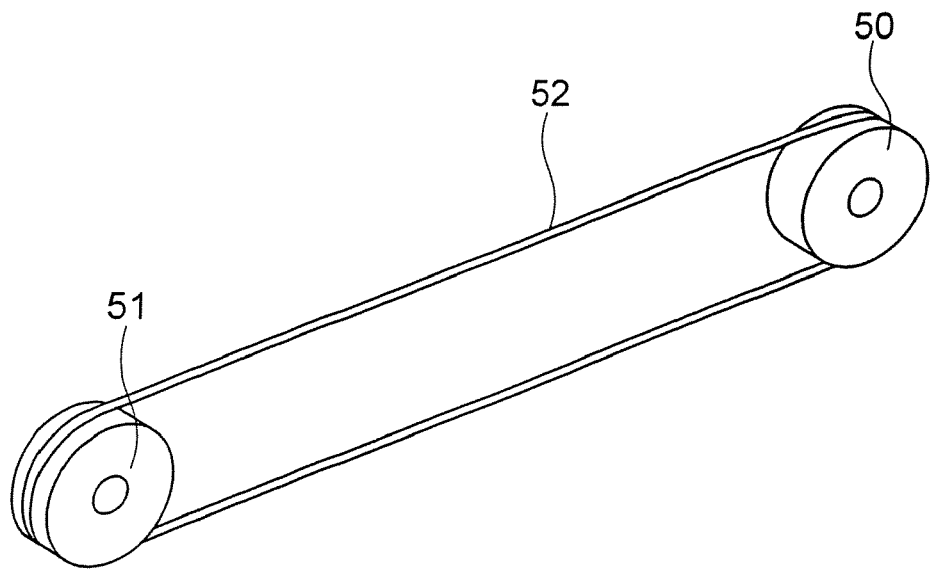
FIG. 28 is a perspective view of the conventional manipulator, which illustrates a relation between a wire and pulleys.

Although the conventional system locates the motors 54 to lie in the horizontal direction as shown in FIG. 25 in the basic attitude of the manipulator, and it invites degradation of controllability because of bad balance of weights. The instant embodiment, however, orients the drive pulley 50 and the driven pulley 51 with the twist of 90 degrees relative to each other so that the center of gravity of each motor 54 comes downward when the manipulator takes the basis attitude. Therefore, the manipulator is well balanced in weight, and therefore excellent in controllability. FIG. 16 shows a relation between the wire 52 and the pulleys 50, 51. The manipulator shown in FIG. 17 has the degrees of freedom of motion including the common rolling axis, pitching axis and yawing axis. However, here again, it has the twist of 90 degrees between the pulleys 50, 51 as shown in FIG. 18. Combination of components for giving such a twist is not limited to the combination of the drive pulley 50 and the driven pulley 51, but the twist may be given between an interposed idle pulley 51a and the pulley 50 (or 51) as shown in the same FIG. 18.

Figure 19:
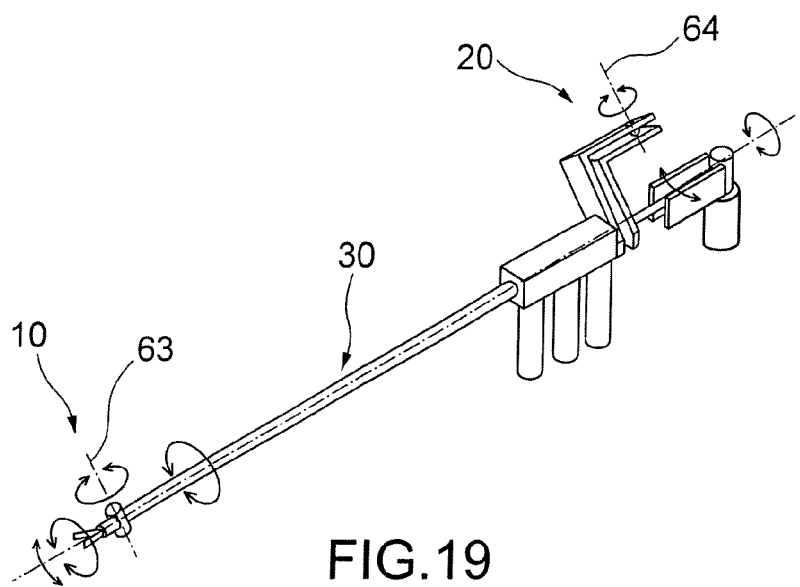
FIG. 19 is a perspective view of the manipulator according to the third embodiment of the invention.
Figure 20:
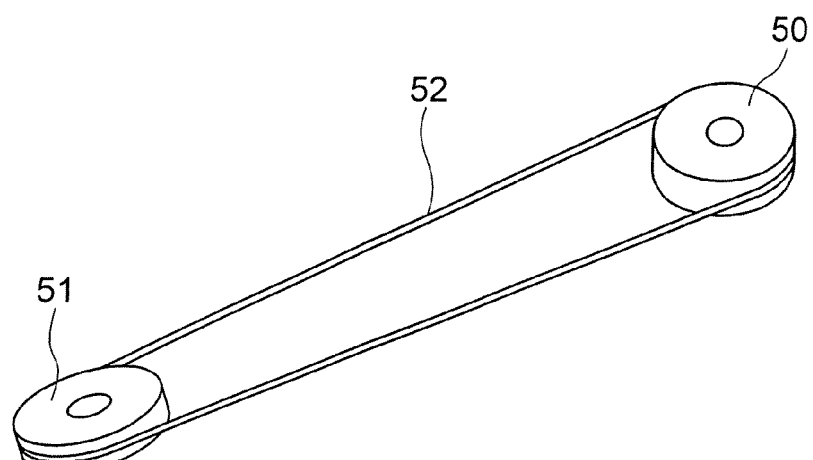
FIG. 20 is a perspective view of the manipulator according to the third embodiment of the invention, which illustrates a relation between the wire and pulleys.
Figure 29:
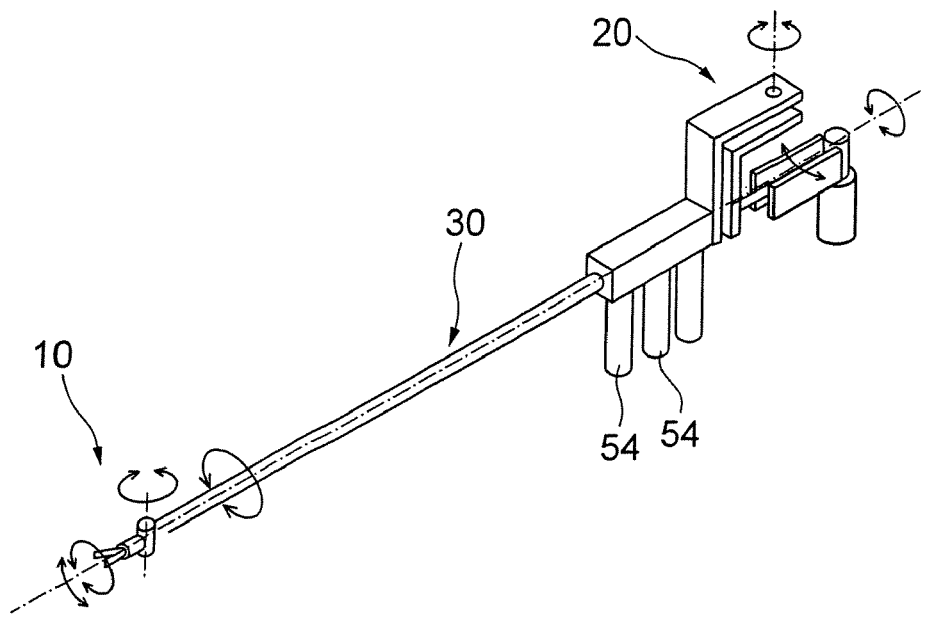
FIG. 29 is a perspective view of a conventional manipulator.
Figure 30:
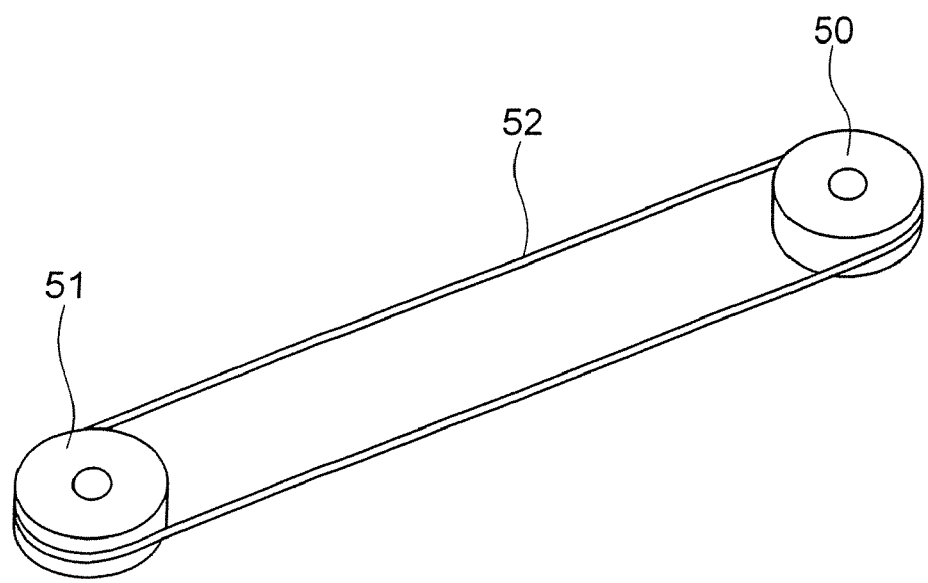
FIG. 30 is a perspective view of the conventional manipulator, which illustrates a relation between a wire and pulleys.
Figure 31:
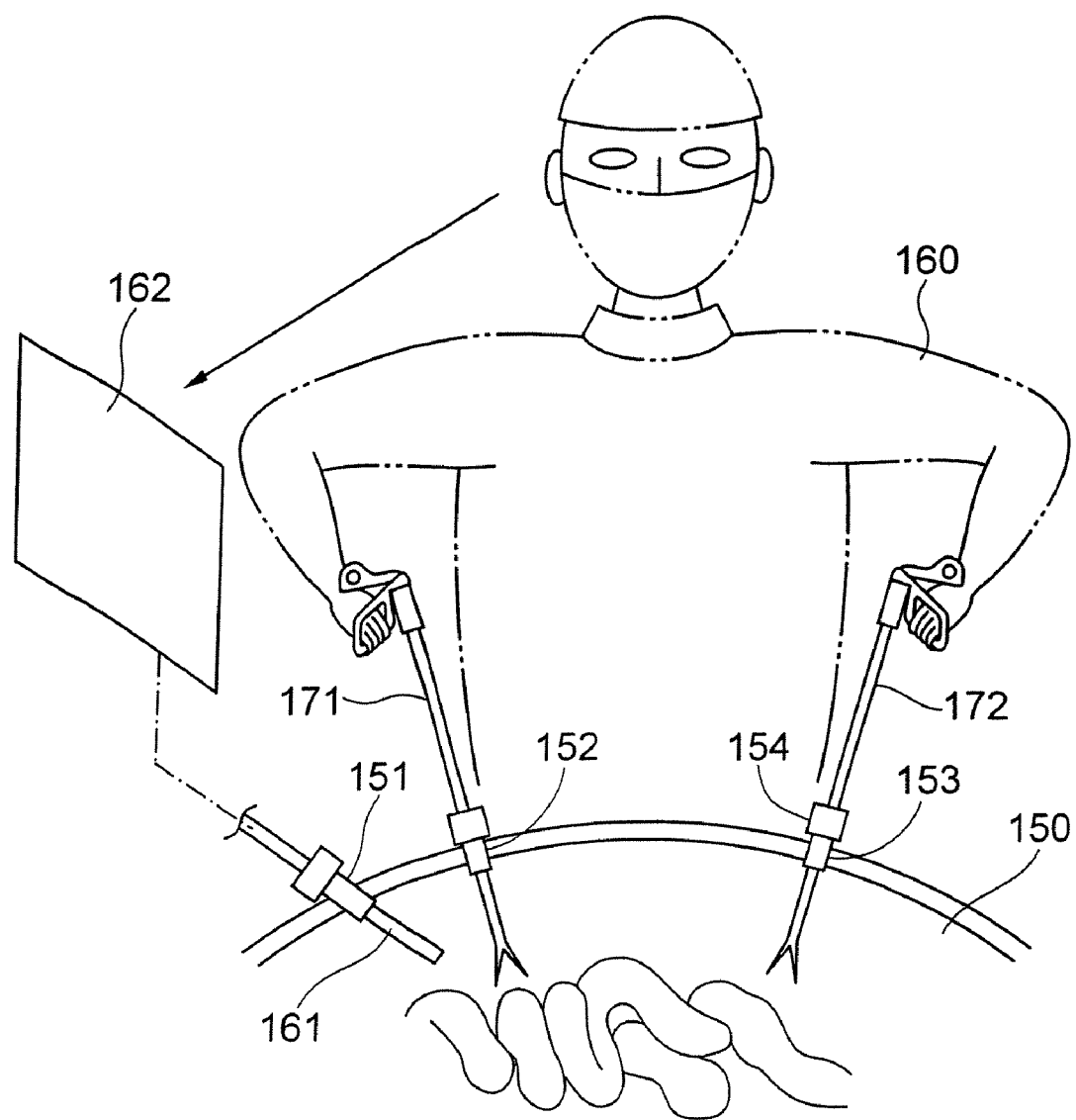
FIG. 31 is a diagram for explaining surgery under a laparoscope.
Figure 32:
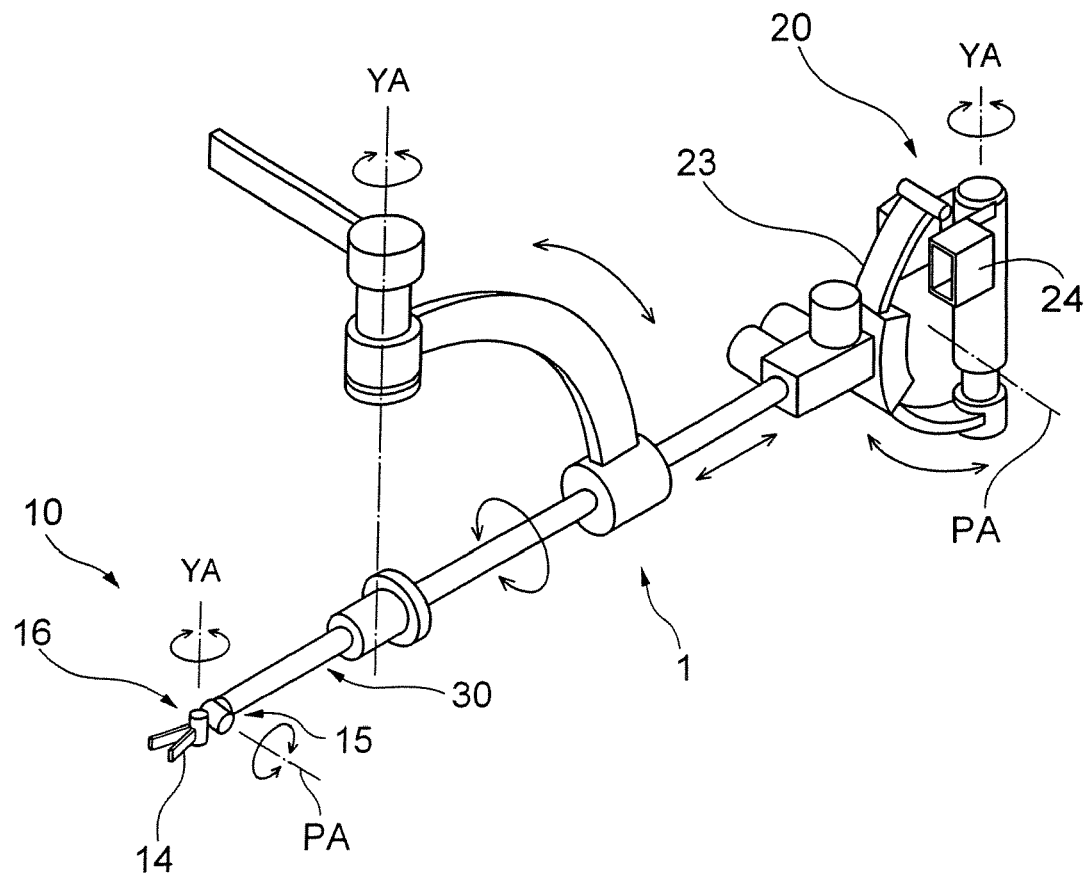
FIG. 32 is a perspective view of a conventional manipulator.
Figure 33:
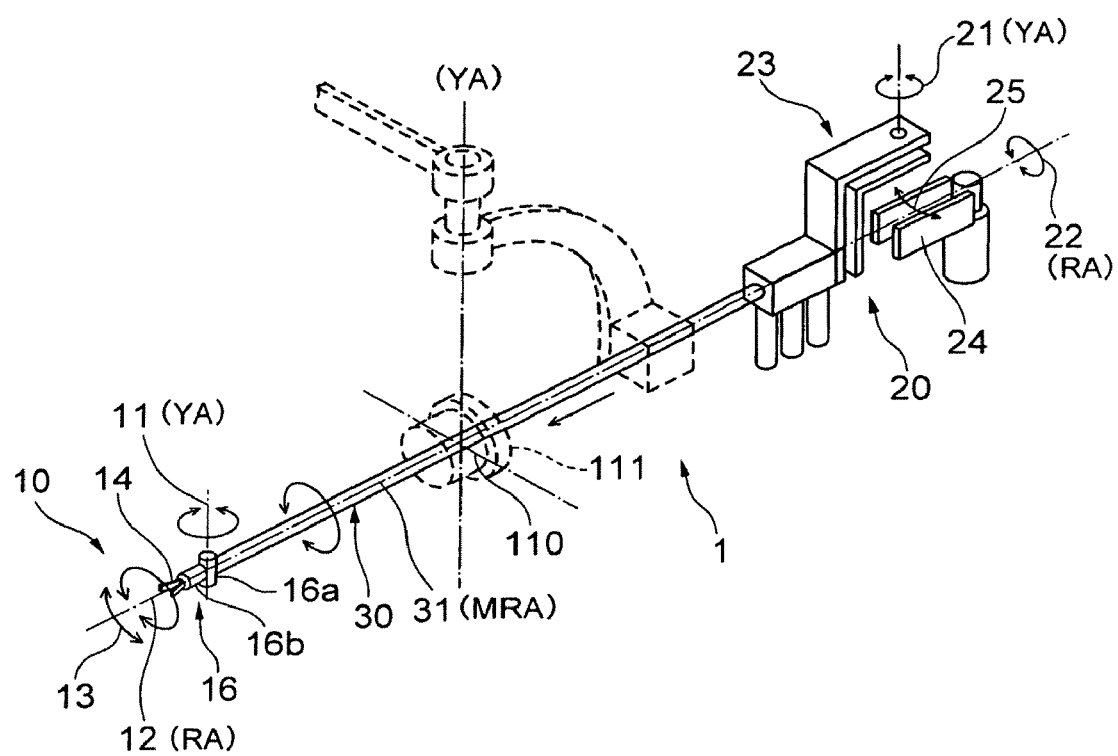
FIG. 33 is a perspective view of a conventional manipulator.

The manipulator shown in FIG. 19 has the degrees of freedom of motion including the common rolling axis, pitching axis of yawing axis, and rolling axis. Here again, the twist of approximately 45 degrees is given between the drive pulley 50 and the driven pulley 51. In this case, the rotation axis 63 of the work unit 10 and the rotation axis 64 of the control unit 20 coincide approximately. In the arrangement and degrees of freedom shown in FIG. 15 having the common rolling axis, pitching axis and rolling axis, it is difficult to change the attitude of the work unit 10 to the yawing direction (lateral direction) from the illustrated basic attitude because of the singular configuration. In the arrangement and degrees of freedom of motion shown in FIG. 29 having the common rolling axis, yawing axis and rolling axis, it is difficult to change the attitude of the work unit to the pitching direction (vertical direction) because of the singular configuration. In actual controls of the manipulator, it is most often to change the attitude of the work unit from the basic attitude to the lateral and vertical directions, and the arrangements for degrees of freedom shown in FIGS. 25 and 29 invite degradation of controllability.

Figure 21:
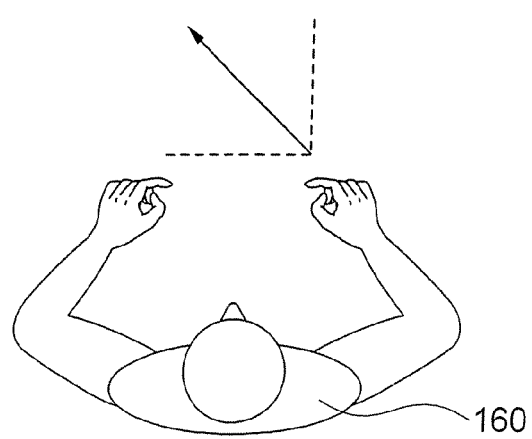
FIG. 21 is a diagram showing a posture of an operator.
Figure 22:
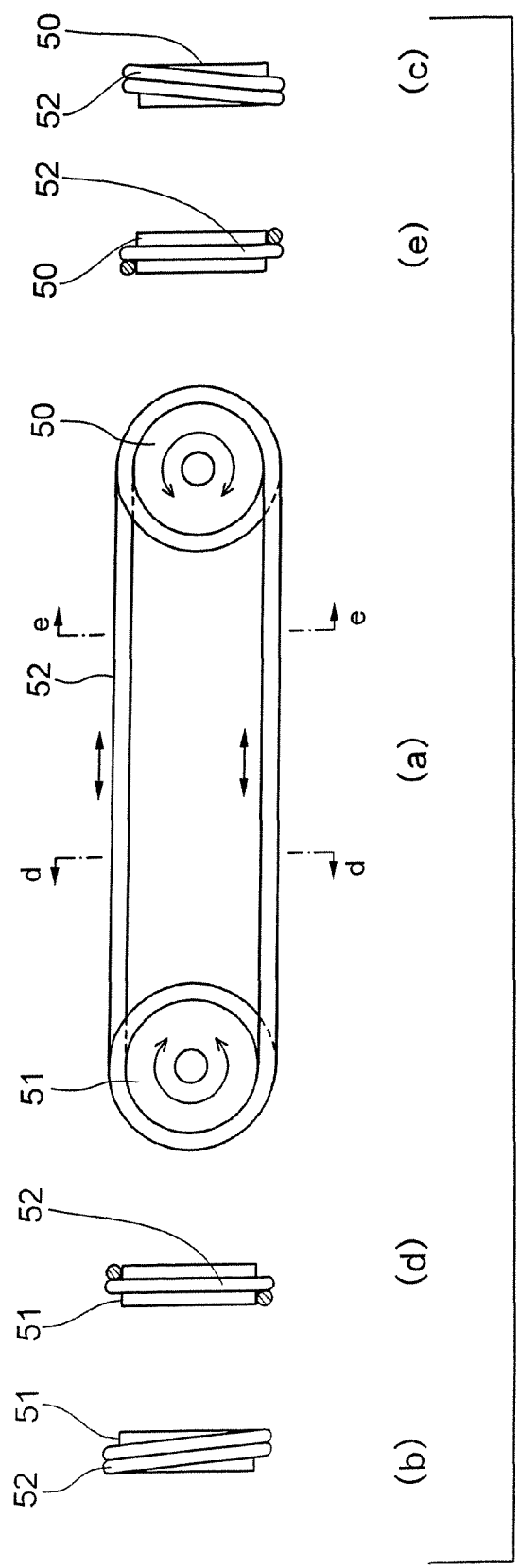
FIG. 22 is a set of a front elevation of a conventional power transmission mechanism, its right and left side elevations, and vertical sectional views taken along the d-d line and the e-e line.
Figure 23:
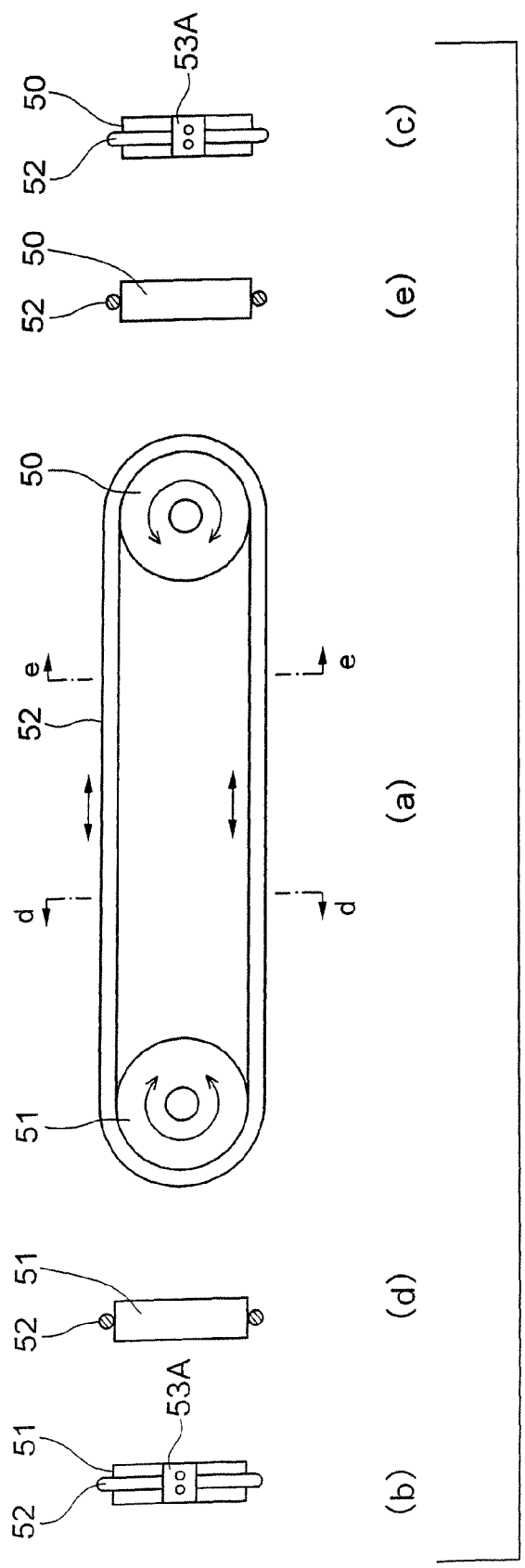
FIG. 23 is a set of a front elevation of a conventional power transmission mechanism, its right and left side elevations, and sectional views.
Figure 24:
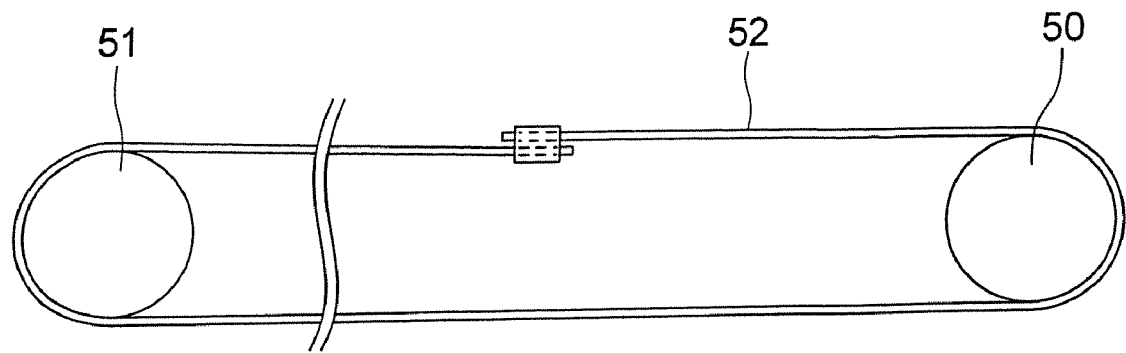
FIG. 24 is a front elevation of the conventional power transmission mechanism.

In laparoscopic surgery, the operator 160 takes the posture shown in FIG. 21 during operation. Therefore, the most natural orientations of the operator's hands are approximately 45 degrees inward respectively. Therefore, the embodiment shown in FIG. 19 having the arrangement of degrees of freedom including the common rolling axis, intermediate direction between the pitching axis and the yawing axis (aslant by 45 degrees approximately) and rolling axis, it is possible to coincide the easiest orientation to control the manipulator with the most natural orientation of a hand of the operator, and simultaneously, the motor 54 having a heavy mass can be placed to orient downward. Therefore, this manipulator minimizes the fatigue of the operator, and its controllability is significantly enhanced. Relative inclination between the two pulleys 50, 51 need not be 45 degrees. Instead, only when it is offset from the pitching axis direction and yawing axis direction even by a slight amount, controllability of the manipulator is improved because the up-and-down direction and the right-and-left direction are offset from the singular configuration.

Furthermore, it is also possible to employ a structure capable of freely giving a desired twisting degree between the drive axis pulley and the driven axis pulley such that the motor comes in a lower area when the manipulator takes the basic attitude optimum for the intended work.

According to the invention, the power transmission mechanism using a wire and pulleys needs no special mechanism for adjusting the tensile force required in conventional frictional drive systems, and has the structure in which the wire does not interfere with the portion for firmly holding the wire on the pulleys. Therefore, the power transmission mechanism meets the requirements of space saving and multiple rotations. Further, the fastening force is enhanced by the wedge effect. Accordingly, the motion region of the manipulator junction, i.e. the work area of the end effector, is wide enough to allow smooth works. Therefore, the manipulator is greatly improved in fidelity to intended works and in controllability.

In addition, since at least one of two spans of the wire (the span of the wire subjected to higher tensile force) between the drive pulley and the driven pulley is covered by a hollow tube or connected by a solid cord, influence of elastic deformation (expansion) of the wire is small enough to assure transmission of sufficient power even when the wire is thin, or the drive pulley and the driven pulley are apart by a long distance. Further, in the hold mode where the drive pulley is stationary or in a servo lock mode, sufficient rotational rigidity is obtained at the driven shaft (output shaft). Therefore, reliable power transmission is assured, and the manipulator is greatly improved in fidelity to intended works and in controllability.

Moreover, since the manipulator has the configuration free from rotational torque caused by eccentric mass about the connector unit in the basic attitude of the manipulator, which is the most standard attitude in the initial status at the start of controls or during controls, the manipulator is enhanced in fidelity to intended works and in controllability without compelling the operator to exert useless control force. Furthermore, the degrees of freedom of motion have the common rolling axis by the connector unit, bent axis in the aslant direction between the yawing axis (lateral direction) and the pitching axis (vertical direction), and rolling axis. Therefore, it is easy to change the attitude of the work section from the basic attitude, and the manipulator is significantly improved in fidelity to intended works and in controllability.

That is, it is possible to provide a power transmission mechanism that is compact, lightweight, reliable, rigid and inexpensive, and by incorporating the power transmission mechanism, it is possible to provide a manipulator for assisting surgery or repairing narrow portion in energy devices, which is enhanced in controllability and in fidelity to intended works.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concepts as defined by the appended claims and their equivalents.

The invention claimed is:

1. A medical manipulator, comprising:
   a working unit configured to perform operations;
   an operating unit configured to generate instructions;
   a drive unit configured to drive the working unit based on instructions given thereto by the operating unit;
   a power transmission mechanism configured to transmit driving force of the drive unit to the working unit;
   wherein the power transmission mechanism includes:
      a flexible power transmission element;
      a pair of a drive pulley and a driven pulley on which the flexible power transmission element is wound, one of the drive pulley and the driven pulley having a pin-embedding hole formed to extend from the outer circumferential thereof toward the center thereof, and a slit elongated in the circumferential direction of the pulley to extend to opposite sides of the embedding hole and communicating with the embedding hole, the slit embedding the flexible power transmission element wound on part of the outer circumferential thereof; and
      an anchor pin having a path hole penetrating the anchor pin across the lengthwise direction thereof to receive the flexible power transmission element inserted therein, the anchor pin fixing one of the pair of the drive pulley and the driven pulley, and the path hole being formed in the slit,
   wherein at least one of said pin-embedding hole and said anchor pin has a tapered shape, the anchor pin receiving the flexible power transmission element in the path hole thereof is embedded in the embedding hole of the associated pulley under pressure, and the flexible power transmission element is thereby held on the pulley.

2. The medical manipulator according to claim 1, wherein the anchor pin is made of an elastic material and reduces its diameter when compressed.

3. The medical manipulator according to claim 1, wherein the outer diameter of the anchor pin is larger than the diameter of the embedded hole of the pulley.

4. The medical manipulator according to claim 1, wherein the slit of the pulley extends substantially parallel with a tangential line of a point on the outer circumferential surface of the pulley.

5. The medical manipulator according to claim 1, wherein the path hole of the anchor pin includes a slit portion extended along the axial direction of the anchor pin to permit the path hole to reduce the diameter thereof when inserted in the embedding hole under pressure.

6. The medical manipulator according to claim 5, wherein the slit portion of the path hole in the anchor pin extends to one or both of the upward direction and the downward direction along the axial direction of the anchor pin.

7. The medical device manipulator according to claim 6, wherein the slit portion extends upward along the axial direction of the anchor pin and penetrates the top surface of the anchor pin to divide it.

* * * * *